(12) United States Patent
Pisoni et al.

(10) Patent No.: US 7,398,677 B2
(45) Date of Patent: Jul. 15, 2008

(54) PROCESS AND EQUIPMENT FOR DETERMINING THE ALCOHOLIC STRENGTH OF A WATER/ALCOHOL SOLUTION

(75) Inventors: Giuliano Pisoni, Pergolese (IT); Vittorio Guarnieri, Trento (IT); Giorgio Umberto Pignatel, Trento (IT)

(73) Assignee: Fondazione Bruno Kessler, Trento (IT)

( * ) Notice: Subject to any disclaimer, the term of this patent is extended or adjusted under 35 U.S.C. 154(b) by 678 days.

(21) Appl. No.: 10/804,083

(22) Filed: Mar. 19, 2004

(65) Prior Publication Data

US 2004/0185151 A1    Sep. 23, 2004

(30) Foreign Application Priority Data

Mar. 21, 2003    (IT)    ........................... TO2003A0210

(51) Int. Cl.
*G01N 11/00*    (2006.01)
(52) U.S. Cl. ..................................... 73/53.01; 73/61.46
(58) Field of Classification Search ................ 73/61.46, 73/53.01
See application file for complete search history.

(56) References Cited

U.S. PATENT DOCUMENTS

| | | | |
|---|---|---|---|
| 3,896,659 A | | 7/1975 | Goodman |
| 4,313,338 A | * | 2/1982 | Abe et al. ................... 73/31.06 |
| 4,362,765 A | * | 12/1982 | Abe et al. ................... 427/535 |
| 5,204,262 A | | 4/1993 | Meiering et al. |
| 6,130,098 A | * | 10/2000 | Handique et al. ............ 436/180 |
| 6,241,663 B1 | * | 6/2001 | Wu et al. ...................... 600/310 |
| 6,301,521 B1 | | 10/2001 | Chen et al. |
| 6,654,620 B2 | * | 11/2003 | Wu et al. ...................... 600/310 |
| 6,766,817 B2 | | 7/2004 | da Silva |
| 6,911,183 B1 | * | 6/2005 | Handique et al. ............ 422/102 |
| 6,939,515 B2 | * | 9/2005 | Carlson et al. ............... 422/101 |
| 7,004,184 B2 | * | 2/2006 | Handique et al. .............. 137/1 |

FOREIGN PATENT DOCUMENTS

| | | |
|---|---|---|
| EP | 0 074 415 A | 3/1983 |
| EP | 0 281 263 A | 9/1988 |
| EP | 0 780 641 A | 6/1997 |
| FR | 2 713 950 A | 6/1995 |
| JP | 1 250 860 A | 10/1989 |
| JP | 10 123 086 A | 5/1998 |
| WO | WO 93/17324 A | 9/1993 |

* cited by examiner

*Primary Examiner*—Hezron E. Williams
*Assistant Examiner*—Rodney T Frank
(74) *Attorney, Agent, or Firm*—Sughrue Mion, PLLC

(57) ABSTRACT

The process comprises the operations of: effecting heating of a predetermined quantity of water/alcohol solution until it partly or completely evaporates, detecting the change in its temperature over time during heating and evaporation of the said quantity of solution, and, determining the total energy necessary to bring about partial or complete evaporation of the said quantity of solution, or the time necessary for partial or complete evaporation, or the integral of that temperature over time during partial or complete evaporation, the value of each of these quantities being indicative of the alcohol concentration by volume in the water/alcohol solution.

16 Claims, 7 Drawing Sheets

Figure 1:
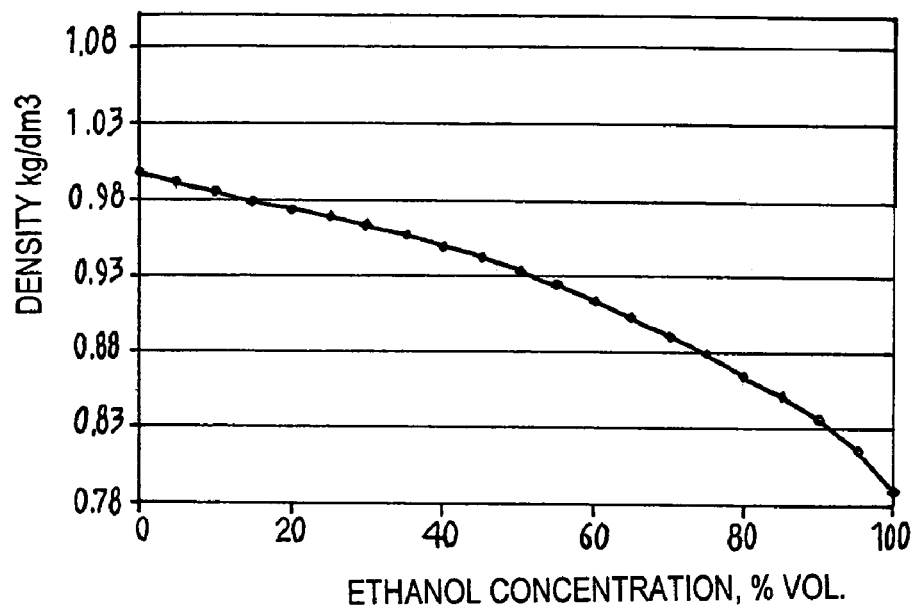

PROCESS AND EQUIPMENT FOR DETERMINING THE ALCOHOLIC STRENGTH OF A WATER/ALCOHOL SOLUTION

BACKGROUND OF THE INVENTION

This invention relates to a process and equipment for determining the alcoholic strength (alcohol concentration by volume) of an alcoholic beverage and water/alcohol solutions in general.

Various parties have an interest in determining the alcoholic strength of water/alcohol solutions.

Manufacturers of such beverages contract for the price of the materials from which they obtain distillates on the basis of alcoholic strength, for example the alcoholic strength of the wine used to produce brandy or the beer used to produce whisky. In addition to this, alcoholic strength is an important parameter in the process in distilleries, as the thermodynamic equilibria in the distillation columns are linked to it.

Also final consumers have a right to know the percentage of alcohol present in the drinks which they are purchasing.

Historically the first instrument for the measurement of alcoholic strength in a water/alcohol solution was Baumé's areometer, which was conceived in 1770. Two centuries later Baumé's areometer is still the most widely used instrument, particularly for measuring the alcoholic strength of distillates.

Baumé's areometer is nothing other than a density meter, in that the principle of its operation is based on the density of the water/alcohol solution being analysed. Water and ethyl alcohol have different densities, specifically 0.998 kg/l for water and 0.789 kg/l for alcohol at 20° C., and their mixtures therefore have densities lying between these two values.

Areometers are direct reading devices and comprise a graduated tube, generally of glass, ballasted in such a way that it adopts a vertical position of stable equilibrium when immersed in a liquid. The hydrostatic thrust (Archimedes thrust) from the water/alcohol mixture against the instrument determines the point at which the graduated tube emerges, directly indicating the alcoholic strength of the solution. This thrust is proportional to the volume of liquid occupied by the immersed body, multiplied by the density of the liquid itself. In order to obtain a direct reading the instrument must be calibrated against a graph relating density with alcohol concentration which (in the case of ethyl alcohol) has the shape shown in FIG. 1 of the appended drawings. As will be seen in that figure, the change in the density of a water/alcohol solution is one which regularly decreases, but is not linear in relation to concentration.

This constitutes a limitation for areometers. In order to overcome these problems precision areometers have a graduated scale restricted to between two not too distant values of alcoholic strength. In order to be able to make measurements throughout the range of values it is therefore necessary to have a set of areometers, each of which is intended for a particular specific range of alcoholic strength. Furthermore, as is the case with almost all substances, density changes in relation to temperature. In the- case of areometers this parameter constitutes a third variable which has to be taken into account. Normally areometers are calibrated at 20° C. and use must be made of adjustment tables, generally provided by the same manufacturer, for all temperature values differing from that reference value.

One form of development of areometers is represented by hydrostatic balance devices. These also determine the density of the liquid by measuring the hydrostatic thrust which the liquid exerts on an immersed glass bulb. This bulb, which contains a capillary thermometer within it, is hooked onto a precision balance through a metal wire. The density of the liquid can be obtained by reading the value of the hydrostatic thrust from the balance, allowing for temperature through suitable conversion tables.

Hydrostatic balance devices are very much more accurate instruments than areometers, but they are also more cumbersome and costly. They require a very stable supporting bench which is not subject to vibration of any kind. These are therefore items of equipment which are intended almost exclusively for laboratory use.

A further instrument which can be used to determine the alcoholic strength of a solution is a pycnometer, which comprises a small glass ampoule provided with a neck and a ground cap with a capillary hole. Using this instrument it is possible to take precisely known and identical volumes of distilled water and the solution whose density is to be determined. Through simple weighings carried out at a particular constant temperature using a precision analytical balance the weight of the empty pycnometer, the weight of the distilled water and the weight of the pycnometer with the solution under test are determined. The relative density of the solution under investigation, that is the density in relation to that of water, can then be calculated using a simple formula.

Around 1850, approximately one century after the invention of the Baumé areometer, another instrument to determine the alcoholic strength of a solution appeared—the Malligand ebulliometer or ebullioscope. This instrument makes use of the property that water/alcohol mixtures have different boiling points depending on the quantity of alcohol which they contain.

The Malligand ebulliometer comprises a metal boiler connected beneath to an annular tube which is inclined and welded to a small chimney beneath which a heating lamp is positioned. This annular tube makes it possible for the liquid present in the boiler to be heated by thermal siphoning. The boiler is closed with a screwed lid provided with holes and has a metal arm bent into a right angle. A thermometer passes through the central hole in the lid and its bulb dips into the boiler while its capillary, which is also bent into a right angle, is housed horizontally in a metal arm, against a graduated scale. A cooling unit, whose function is to cause condensation of the alcoholic vapours to prevent any change in concentration of the solution altering the boiling point, is housed in the side hole of the cover.

When making measurements the ebulliometer is filled with the solution under investigation, the lid is screwed on and the cooling device filled with water is fitted. Heating then begins and the maximum temperature reached is read off. This coincides with a graduation on the alcoholometric scale, which provides the alcoholic strength directly.

Alcoholic beverages obtained by distillation, like brandies, can be regarded as pure water/alcohol solutions from the physical point of view, that is they comprise a mixture of water and ethyl alcohol. All the other components, although important from the organoleptic point of view, are present in quantities which are too small for them to have an influence on the measurement of alcoholic strength.

Figure 2:
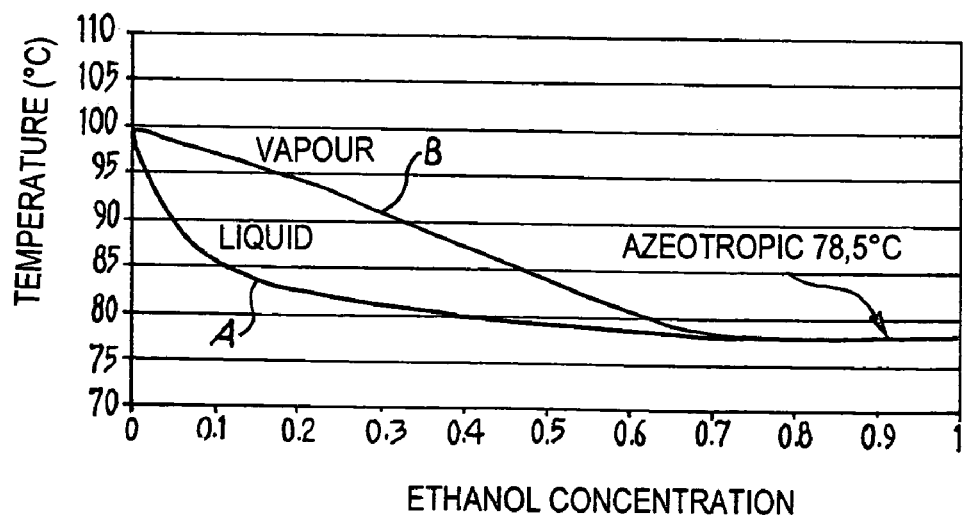

In the case of drinks with a low alcohol content, like wines, the presence of other components like tannins, acids, etc., may result in incorrect measurement of the alcoholic strength when densitometric methods are used. In such circumstances the Malligand ebulliometer offers considerable advantages. In fact this instrument measures the boiling point of the solution under investigation and this measurement is more accurate the lower the alcoholic strength. FIG. 2 in the appended drawings shows the binary phase diagram for water/ethanol. The lower curve A, also known as the liquidus curve, represents the boiling points of the mixture; the upper curve B instead shows the composition of the vapour in equilibrium with the boiling liquid. It will be noted that boiling curve A has a much greater slope for low alcohol concentrations. For this reason the Malligand ebulliometer provides better accuracy up to alcohol concentrations of 20%.

Measurements made using a Malligand ebulliometer are approximate, but have the advantage of being quick to obtain. This instrument cannot however be used with solutions containing sugars, like liqueur wines, or carbon dioxide, like sparkling wines, because these substances have an appreciable effect on the boiling point. In these cases it is first necessary to perform a distillation of the beverage to purify it from the undesired substances and then measure the alcoholic strength.

SUMMARY OF THE INVENTION

One object of this invention is to provide a process for determining the alcoholic strength of a water/alcohol solution which requires the use of a minimum quantity of solution, and which makes it possible to measure the alcoholic strength accurately and quickly, requiring a minimum quantity of energy for the purpose.

Another object of this invention is to provide a device for determining alcoholic strength which has a relatively low cost of manufacture, particularly in respect of large production volumes, and of small size and low energy requirement so that it can also be used in a portable form.

The abovementioned objects, and yet others, are achieved according to the invention through a process whose salient characteristics are defined in appended claim 1, and using a device whose characteristics are defined in claim 9.

BRIEF DESCRIPTION OF TILE DRAWINGS

Figure 3:
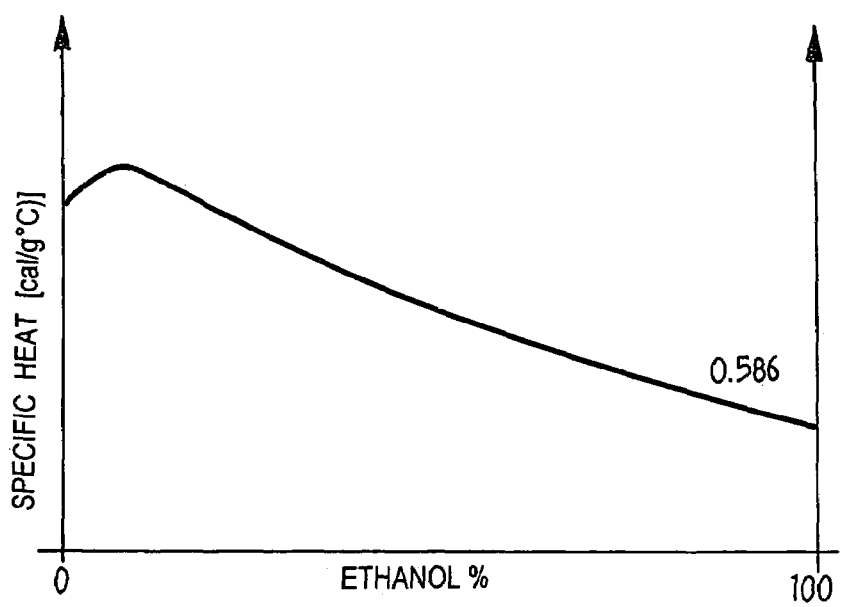
Figure 4:
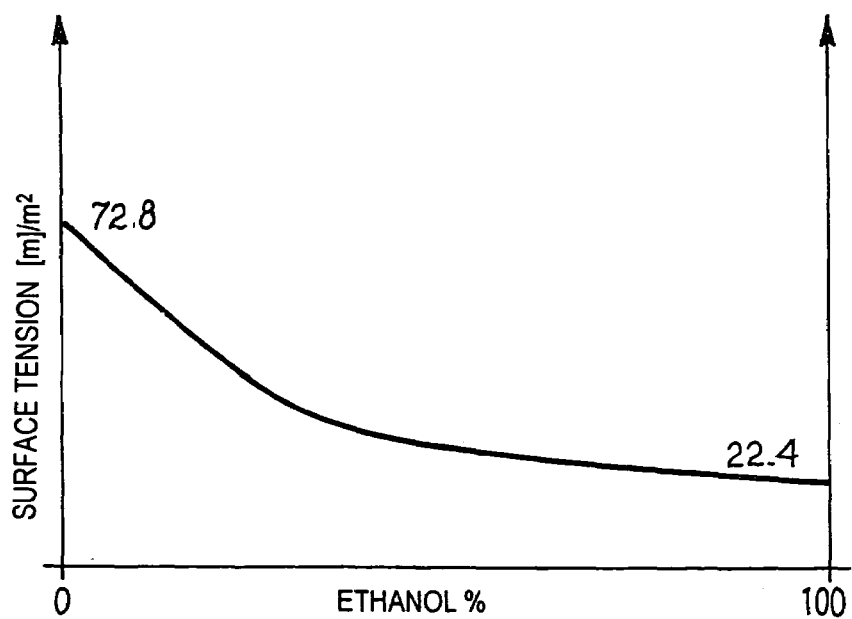
Figure 5:
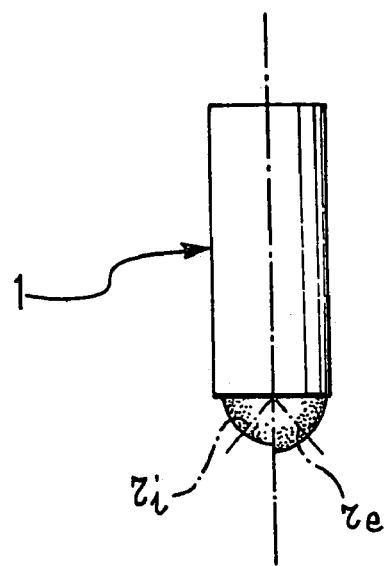
Figure 6:
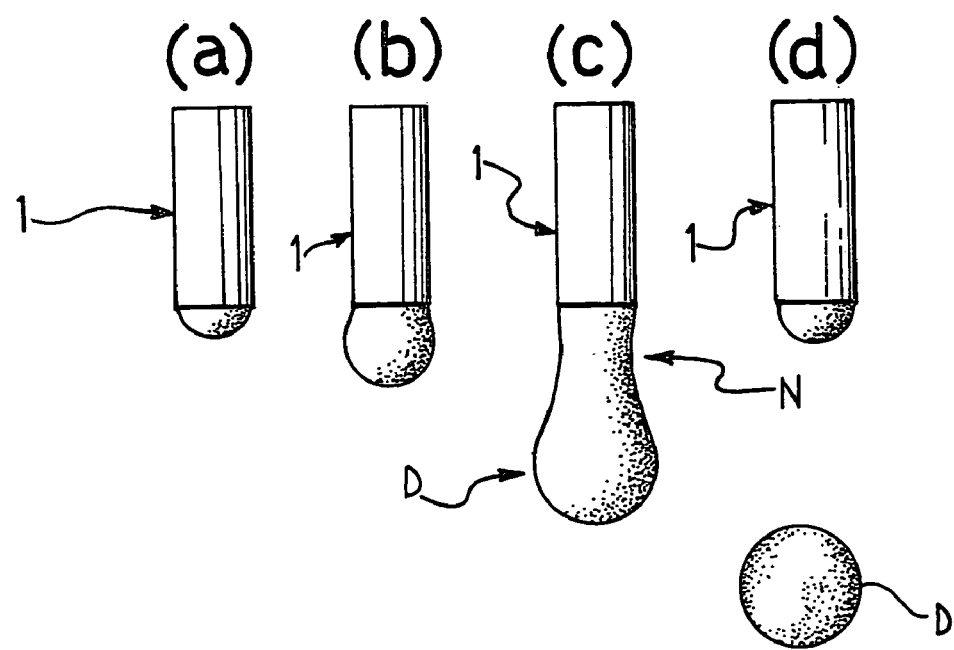
Figure 7:
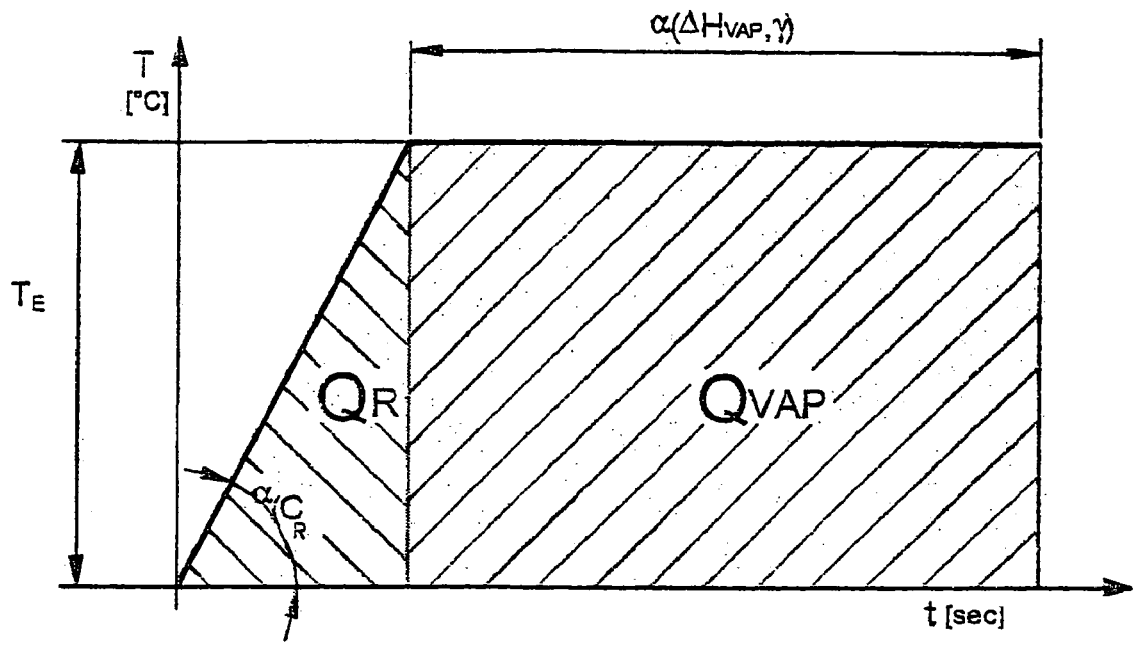
Figure 8:
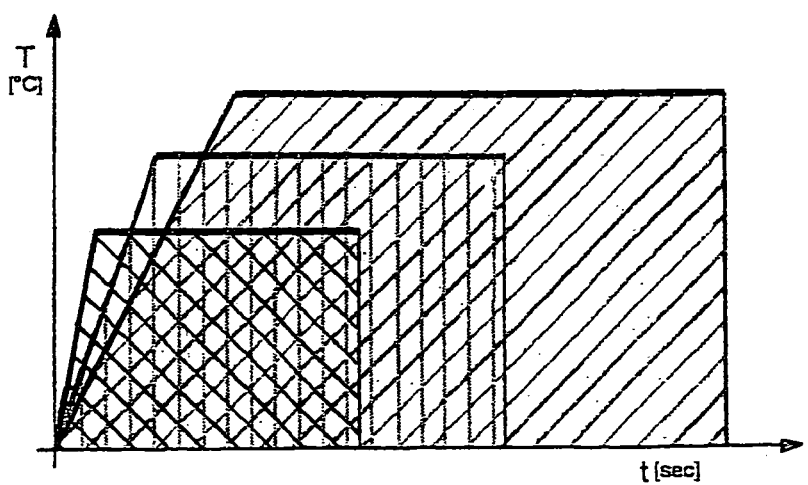
Figure 9:
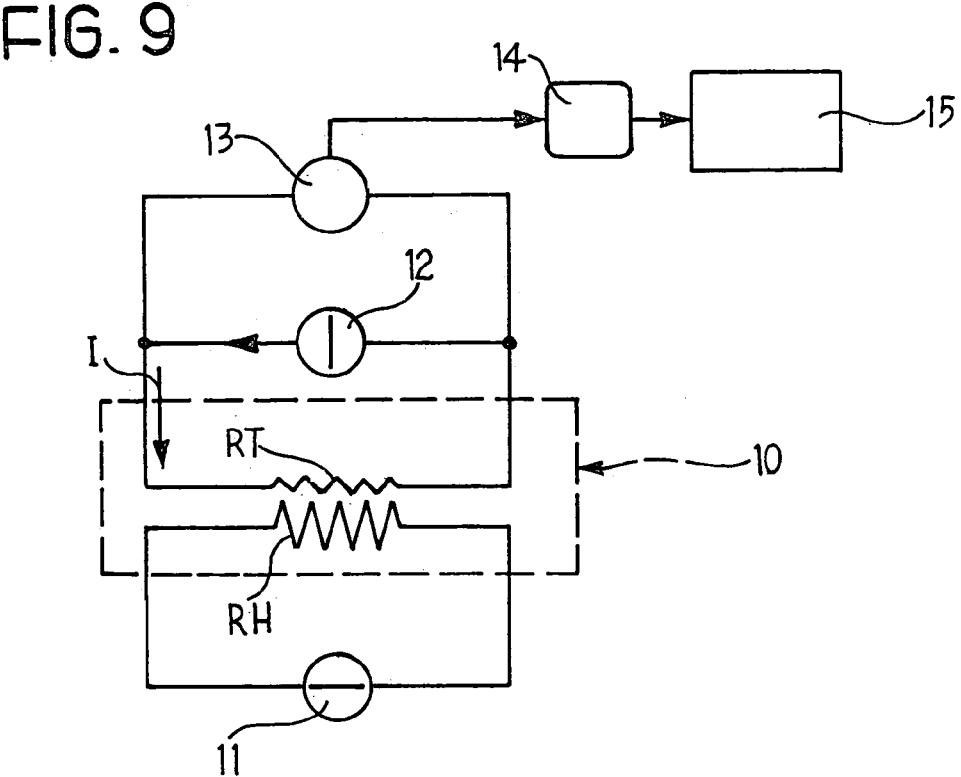
Figure 10:
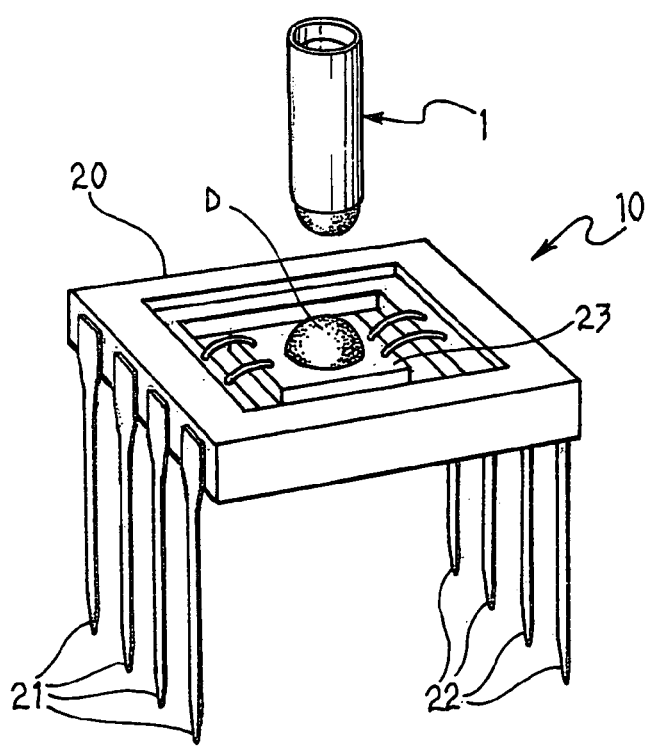
Figure 11:
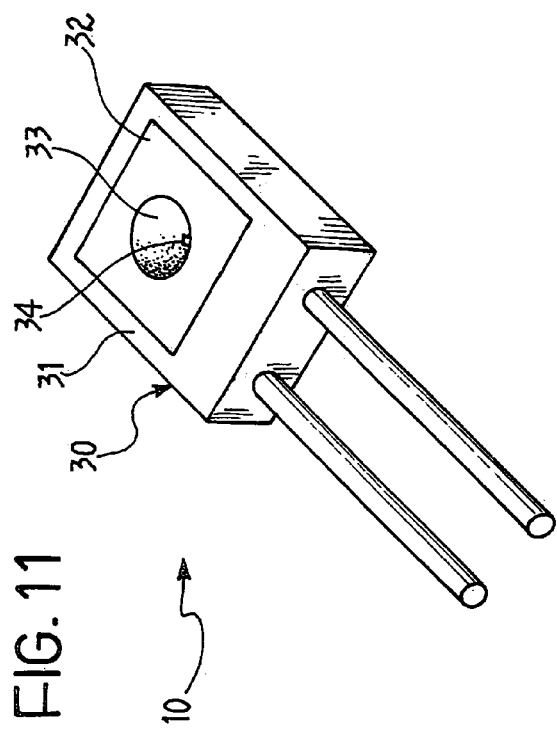
Figure 12:
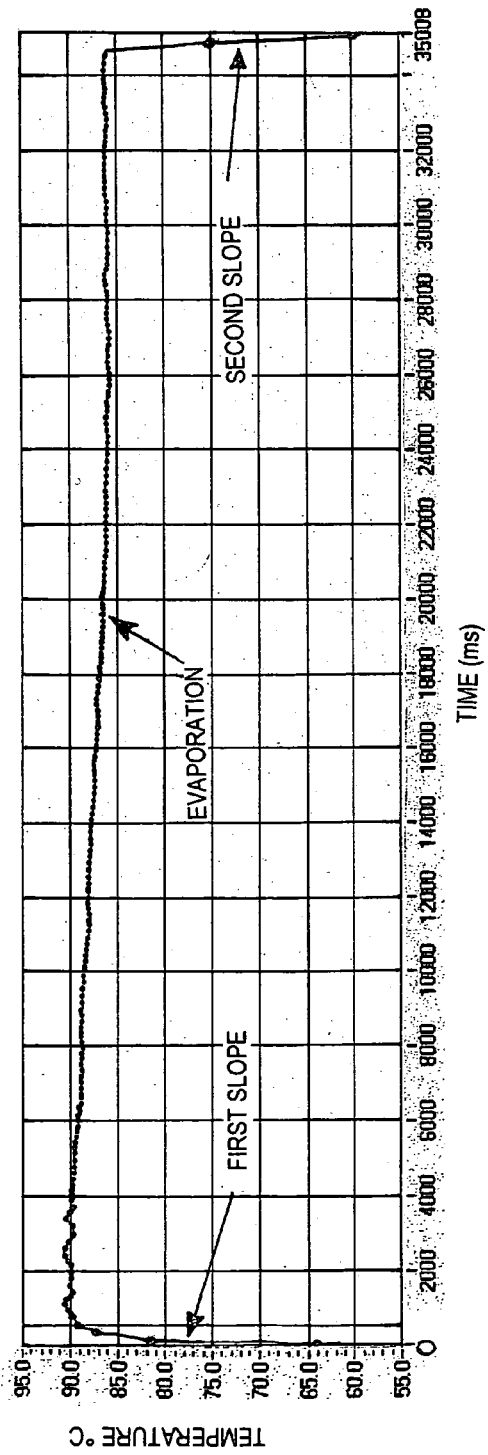
Figure 13:
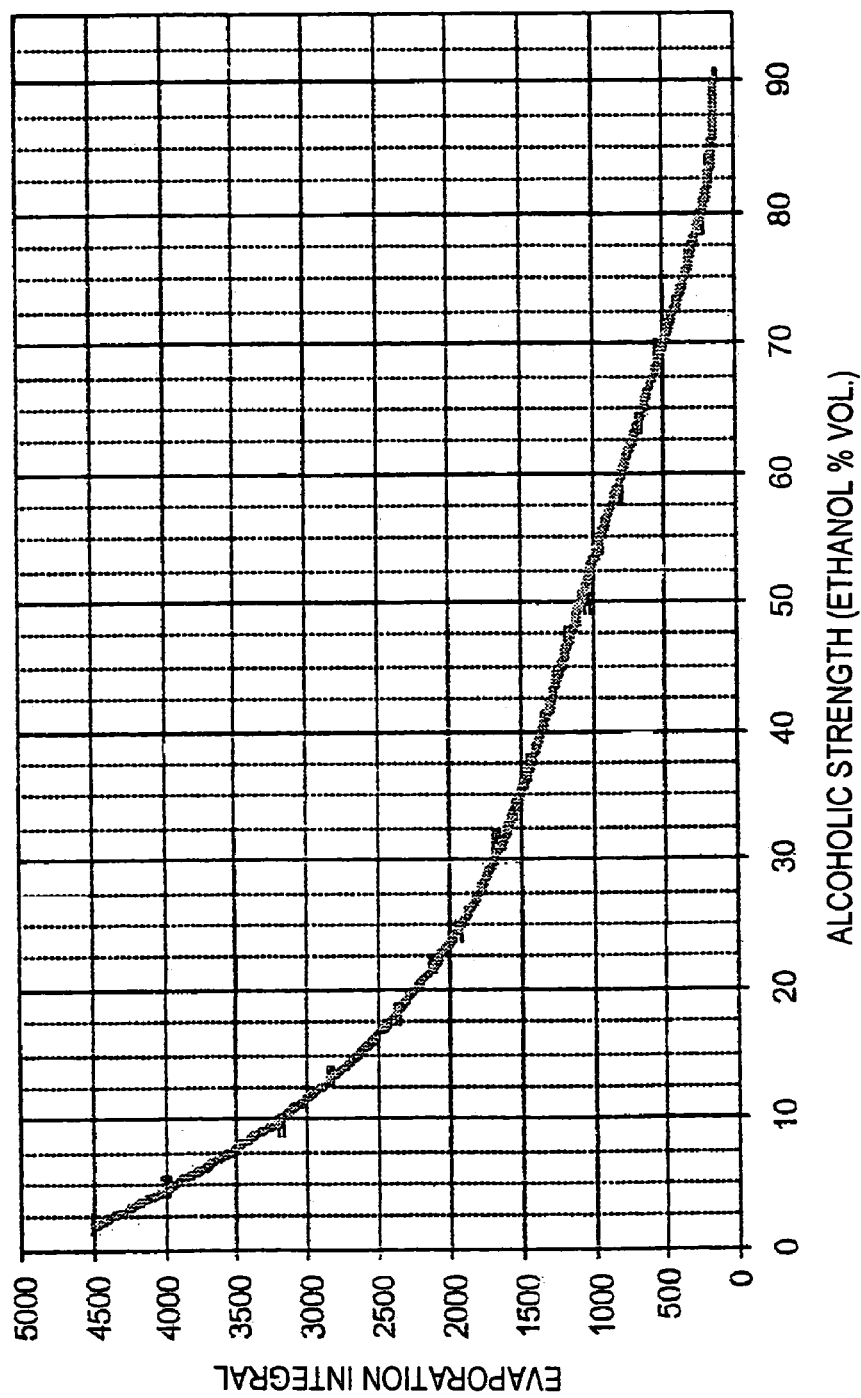

Further features and advantages of the invention will appear from the detailed description which follows, provided purely by way of a non-restrictive example, with reference to the appended drawings, in which:

FIGS. 1 and 2, already described, are graphs showing the changes in density and boiling point of a water/alcohol solution, FIGS. 3 and 4 are graphs showing the change in the specific heat and surface tension of a water/alcohol solution in relation to the percentage content by volume of ethanol, FIG. 5 shows a capillary tube used in the process according to the invention to form a drop of water/alcohol solution, FIGS. 6 (a), (b), (c) and (d) are four views showing a sequence in the formation and detachment of a drop using a capillary tube, FIGS. 7 and 8 are graphs which show examples of changes in the temperature of a drop of water/alcohol solution during the heating and evaporation stage as a function of time t shown as the abcissa, FIG. 9 is an electrical diagram, partly in block form, which shows part of a device used to implement the process according to the invention, FIG. 10 is a diagrammatical illustration of a perspective view showing part of a device according to the invention, FIG. 11 is an illustration in perspective of a variant embodiment of part of the device according to the invention, FIG. 12 is a graph showing an example of changes in the temperature of a drop of water/alcohol solution over time when heating and evaporating in a device according to the invention, and FIG. 13 is a graph showing the change in the integral of the temperature of a drop of water-alcohol solution during heating and complete or partial evaporation as the alcoholic strength of the solution changes.

DETAILED DESCRIPTION OF THE INVENTION

Alcohols, and in particular ethyl alcohol, have various physical properties which are quantitatively different from the corresponding properties of water. Among these properties, as has been mentioned previously, there are the density (see FIG. 1) and the boiling point (see FIG. 2).

Other physical properties of the said liquid substances can be considered with the view to developing new methods/devices for determining the alcoholic strength of a water/alcohol solution. These include the specific heat, the surface tension and, at least hypothetically, the latent heat of evaporation.

Water and alcohols in fact have different specific heats, and their mixtures have specific heats which vary between the two values for the pure substances, as shown in FIG. 3 (for ethyl alcohol). It will however be seen from this figure that at low ethanol concentrations the relationship between specific heat and ethanol concentration is not uniform and is not therefore unequivocal.

Likewise, water and ethanol in the pure state have very different respective surface tension values, as may be seen from observing the ends of the curve shown in FIG. 4. Furthermore the change in the surface tension of their mixtures varies rather little for concentrations above 35%.

Values for the latent heat of evaporation of water and alcohols in the pure state also differ appreciably. Ethanol (for example), in addition to having a very low boiling point, has a latent heat of evaporation which is less than half of that of water. However, it is rather difficult, to define a latent heat of evaporation value for a mixture of these substances. In fact when a two component mixture begins to boil the vapour which is initially released is richer in the more volatile component (alcohol in the case of a water/alcohol solution). Furthermore this is the phenomenon which is made use of in the process of distillation.

The latent heat of evaporation would not therefore at first sight appear to represent a particularly significant parameter from the point of view of developing a new method/device for determining the alcoholic strength of a water/alcohol solution.

As will appear more clearly below, this invention is nevertheless essentially based on the use of this parameter.

In order to determine the alcoholic strength of a water/alcohol solution according to the invention a capillary conduit having a predetermined diameter (0.25 mm, as a non-restrictive example), such as the needle of a syringe, is used, operatively positioned in a vertical position.

A quantity of the water/alcohol solution under investigation is placed in this capillary conduit.

As is known, the weight of a drop formed at the lower end of a capillary conduit is linked to the surface tension of the liquid and the radius of the capillary through Tate's law:

$$mg = 2\pi\gamma r_c \qquad (1)$$

where m is the mass of the drop, g is the acceleration due to gravity, $\gamma$ is the surface tension of the liquid and $r_c$ is the radius of the capillary. With reference to FIG. 5, in which a capillary tube is indicated by 1, if the liquid present in the capillary wets the latter then in Tate's law shown above the radius $r_c$ is the outer radius, that is the radius $r_e$ shown in the left hand part of FIG. 5, while if the liquid does not wet the capillary the aforesaid radius $r_c$ is assumed to be equal to the internal radius of capillary tube 1, indicated by $r_i$ in the left hand part of FIG. 5.

In the process according to the invention a drop of the water/alcohol solution under investigation is caused to emerge from the lower end of the capillary conduit (for example through a syringe), as illustrated indicatively by the sequence in FIGS. 6 (*a*), (*b*), (*c*) and (*d*). While drop D detaches from capillary conduit 1, as can be seen in FIG. 6*c*, a thin neck of liquid indicated there by N, which breaks in half, is formed, and part of the liquid of the drop remains on the lower end of the capillary conduit.

In order to determine the weight of the drop D detached from the capillary it is therefore appropriate to alter the expression for Tate's law by a correction factor f, that is according to the following expression:

$$mg = 2\pi\gamma r_c \cdot f \quad (2)$$

In the process according to the invention a certain quantity of the water/alcohol solution under investigation, for example a drop detached from a capillary conduit as described above, is placed or deposited on a heating device constructed for example in one of the two ways which will be described below. This heating device is activated in a controlled manner so as to bring about heating of the drop of water/alcohol solution until it completely or partly evaporates. During this heating and evaporation of the solution the change in temperature over time is detected in the manner which will be described below, measuring the integral of that function over time, or the time or total energy necessary to bring about complete or partial evaporation of the solution. The value of this parameter is indicative of the concentration of alcohol by volume in the solution under investigation.

In the case where the temperature of this quantity of solution is detected up to partial evaporation of the same, the final instant of the measurement is determined for example by means of a weighing sensor associated with the heating device when a predetermined residual weight of the said quantity of solution on the heating device is reached.

The total energy or heat necessary to evaporate for example one drop of liquid corresponds to the sum of the heat $Q_R$ required for heating from ambient temperature to the boiling point $T_E$, and the heat $Q_{VAT}$ required for evaporation to complete disappearance of the drop.

FIG. 7 shows the theoretical shape of the evaporation curve of a liquid in a temperature/time (T/t) diagram. The hatched area beneath the graph in FIG. 7 is a function of the total heat absorbed by the liquid if the power supplied during heating remains constant. An analytical determination of the total heat of evaporation of a drop of liquid can be obtained assuming as a first approximation that the temperature remains constant throughout all the evaporation, and neglecting the fact that it is a two-component mixture. On the basis of these assumptions we obtain:

$$Q_{TOT} = Q_R + Q_{VAP} \quad (3)$$

where $$Q_R = C_p \cdot m \cdot \Delta T \quad (4)$$

and $$Q_{VAT} = \Delta H_{VAP} \cdot m \quad (5)$$

m being the mass of the drop, $C_p$ being the specific heat of the solution, and $\Delta H_{VAP}$ being the latent heat of evaporation.

According to Tate's law, shown previously:

$$m = \frac{2\pi\gamma r_c}{g} \quad (6)$$

Combining equations from (3) to (6) together we finally obtain:

$$Q_{TOT} = \frac{2\pi\gamma r}{g}(C_p - \Delta T + \Delta H_{VAP}) \quad (7)$$

In equations (4) and (7) $\Delta T$ is $$\Delta T = T_E - T_A \quad (8)$$

where $T_E$ is the boiling point of the liquid and $T_A$ is the ambient temperature.

Using equation (7) above, and attributing the corresponding values relating to pure water and pure ethanol to the various quantities shown therein, an estimate of the two extreme values of the total heat of evaporation $Q_{TOT}$ can be obtained, assuming that the diameter of the capillary from which the drop is obtained is 0.25 mm and that the initial temperature of the drop $T_A$ is 20° C. Thus we obtain for water:

$$Q_{TOT_{H_2O}} = \frac{2 \cdot \pi \cdot 72.8 \cdot 0.25 \cdot 10^{-3}}{9.81}(1 \cdot (100-20) + 540.9) \cong 7.238 \text{ cal}$$

and for ethanol:

$$Q_{TOT_{C_2H_6O}} = \frac{2 \cdot \pi \cdot 22.4 \cdot 0.25 \cdot 10^{-3}}{9.81}(0.586 \cdot (78.3-20) + 209.7) \cong 0.875 \text{ cal}$$

Now the two results shown above differ by almost one order of magnitude. This is due to the fact that surface tension acts on both the terms appearing within the round brackets in equation (7) above.

The change in the $Q_{TOT}$ values of a water/alcohol mixture as a function of alcohol concentration cannot be determined from the outset, as the latent heat of evaporation $\Delta H_{VAP}$, for which experimental graphs are not known, represents approximately 86% of the sum of the terms between brackets in equation (7) in both cases.

FIG. 8 shows qualitatively how change in alcoholic strength acts on the evaporation curves. The hatched areas indicate the total heat of evaporation $Q_{TOT}$ of a drop, that is the integrals of the temperature/time functions, which change as the alcohol concentration of the mixture changes.

As will appear more clearly below, the method for calculating the evaporation integral, or the time or energy of evaporation of a solution, is very interesting from the theoretical point of view, partly because it implicitly involves different physical parameters in the measurement, each of which help to accentuate the differences between water and alcohol, but also because of the simplicity of the measurement. In sum it is a question of integrating a temperature-time function and then converting this result into an indication of alcoholic strength through a calibration curve which has previously been determined by experiment.

By way of example, the diagrams in FIGS. 9 and 10 indicate as a whole a device for heating and the measurement of temperature which is designed to receive a drop of a water/alcohol solution under investigation. This device 10 essentially comprises a heating resistor $R_H$ connected to a power supply 11, which is an AGILENT E3631A power supply capable of providing dual voltages up to 25 V.

A thermistor $R_T$ acting as an electrical temperature sensor is associated with heating resistor $R_H$. A current generator 12, such as for example a Lakeshore 110 generator, is connected to that thermistor and is capable of providing the thermistor with a constant electrical current I of a low amperage.

The voltage at the terminals of thermistor $R_T$ is operatively determined using a voltmeter device 13. A National Instruments Daq Pad 6020E, which provides data indicating the voltage determined at the thermistor terminals to a resistance/temperature converter 14, may for example be used for this purpose. This converter may be operated through a personal computer provided with National Instruments Labview software which makes it possible to record the change in the voltage of thermistor $R_T$ over time. A display device 15 is connected to converter 14.

FIG. 10 shows a first embodiment of the heating and temperature measuring device indicated as a whole by 10 in FIG. 9 described previously.

In the embodiment shown in FIG. 10 device 10 comprises a microheater of a type which is in itself known, for example a microheater of the GAS500 type, currently used as thermal supports for gas sensors. In this case the resistance of heating resistor $R_H$ and the resistance of thermistor $R_T$ are 1.27 Kohm and 8.5 Kohm respectively.

Microheater 23 comprises a single silicon substrate in which, using integrated circuit technology, heating resistor $R_H$ and thermistor $R_T$ are constructed of polysilicon.

With reference to FIG. 10, heating and temperature measurement device 10 comprises a package 20 of electrically insulating material, from which there extend a plurality of connecting pins 21 and 22. The microheater proper, 23, is located in package 20, and its upper active surface or face is intended to have a drop D of water/alcohol solution deposited upon it through a capillary 1.

As mentioned previously, capillary 1 may be the needle of a syringe. In order to be able to dispense the drop precisely in the center of the active surface of microheater 23 the syringe, fitted with the selected capillary, can be advantageously fixed on a burette stand or the like.

FIG. 11 shows a variant embodiment of the heating and temperature detecting device indicated by 10 in FIG. 9.

In the embodiment according to FIG. 11 device 10 comprises a resistor 30, having a package of plastics material 31 surrounding a heating resistance element 32 with an electrical resistance of approximately 2 ohm. Heating resistor 32 projects from one surface of package 30 and in it there is a cavity 33, which is for example essentially hemispherical, acting as a recess to receive and contain a drop of the water/alcohol solution under investigation.

In an experimental device a 2 ohm, 2 W resistor manufactured by RS. Components was used, and in this a recess having a diameter of approximately 3 mm was constructed using a drill bit.

A microthermistor 34 is located at the base of cavity 33. This thermistor must obviously be as small as possible so that it remains covered until the last of the liquid while evaporation is in progress. A thermistor suitable for the purpose is the Small Bead 103 EAJ-H01 thermistor from Fenwal Electronics, Inc., which has an ellipsoidal shape with a larger diameter of approximately 0.5 mm and a lesser diameter of 0.35 mm. This type of thermistor has a negative variation characteristic for resistance as a function of temperature (NTC).

Device 10 in FIG. 11 may be used essentially in connection with the power supply and detection devices described previously with reference to FIG. 9, only changing the voltage applied to heating resistor 32, as its resistance of approximately 2 ohm differs appreciably from the approximately 1 Kohm resistance of the heating resistance of a microheater.

Using a device of the type described above with reference to FIG. 11 it is necessary to bear in mind that, unlike a microheater, heating resistor 32 has a non-negligible thermal inertia, and therefore requires some time to reach steady thermal conditions. It is therefore necessary to wait until the temperature reaches a predetermined value which is the same for all measurements between one measurement and another, that is before dispensing the drop.

FIG. 12 shows the graph of temperature as a function of time measured in relation to the evaporation of a drop of water/alcohol solution, in particular using the second measuring device (FIG. 11) described above. The line showing the change in temperature as a function of time in the graph in FIG. 12 lies between a first and a second almost vertical slope which identifies the start and end of the evaporation of a drop of solution.

Whenever a drop of solution is dispensed, thermistor $R_T$ (34) in the measuring device undergoes sudden cooling, followed by equally sudden heating. The second slope shown in FIG. 12 instead corresponds to the time when evaporation of the drop of solution is exhausted, in that the last quantity of liquid evaporating on the surface of the thermistor absorbs heat from the thermistor itself, which as a consequence cools.

The two slopes in the graph in FIG. 12 can be "recognised" by the recording programme as the start and end of evaporation, that is as the two integration limits of the temperature/time curve. The area subtended by the curve in FIG. 12 graphically represents the integral of temperature T over time t during evaporation of the drop of solution. This integral is a function of the total heat of evaporation $Q_{TOT}$ of the water/alcohol solution.

Through comparing the calculated value of the evaporation integral with a graph or a table previously derived experimentally, such as that shown in FIG. 13, the alcoholic strength of the water/alcohol solution under investigation can be read off immediately.

The graph in FIG. 13 can be conveniently stored in memory in the processing device connected to the heating and temperature detection device 10 used. In this case display device 15 in FIG. 9 can provide a direct reading of the alcoholic strength determined.

As those skilled in the art will appreciate immediately, the method and equipment proposed according to this invention are extremely advantageous.

Experimental tests carried out by the inventors have confirmed that it is possible to obtain measurements of alcoholic strength which are sufficiently accurate over the entire range of alcoholic strength. The accuracy of experimental devices has proved to be approximately 0.50°, but this could be further improved through technological refinements.

Specifically, the advantages offered by the invention in comparison with conventional measurement systems are essentially the following:
- extremely small quantities of solution for measurement (<10 mg),
- good accuracy over the entire range of alcoholic strength (0.5° or less),
- very low energy consumption (<1 W),
- very small dimensions for the device required,
- the possibility of incorporating control electronics, and low manufacturing cost.

Of course, without changing the principle of the invention the embodiments and particulars of construction may be varied widely from what has been described and illustrated purely by way of a non-restrictive example without thereby going beyond the scope of the invention as defined by the appended claims.

What is claimed is:

1. Process for determining the alcoholic strength of an alcoholic beverage or a water/alcohol solution in general, comprising the operations of:
    effecting the heating of a predetermined quantity of the said water/alcohol solution until it partly or completely evaporates,
    detecting the change in its temperature over time as the said quantity of solution is heated and evaporated, and
    determining the total energy necessary to cause partial or complete evaporation of the said quantity of solution, or the time required for partial or complete evaporation, or the integral of the said temperature over time during partial or complete evaporation; the magnitude of each of these parameters being indicative of the alcohol concentration by volume in the said water/alcohol solution.

2. Process according to claim 1, comprising the operations of:
    providing a capillary conduit having a predetermined diameter and containing a quantity of the water/alcohol solution under investigation,
    causing a quantity of the water/alcohol solution to emerge from one end of the capillary conduit, and then depositing that quantity on a heating device.

3. Process according to claim 1, in which the heating device comprises a heating resistor which is operatively provided with constant electrical power and in which the total energy necessary to cause complete or partial evaporation of the said quantity of the water/alcohol solution is evaluated by detecting the change in temperature over time of the said resistor during the period of time between the start of heating the said quantity of the drop of solution on the heater device and complete or partial evaporation of that quantity.

4. Process according to claim 3, in which a temperature sensor, such as a thermistor or a thermocouple, is associated with the said heating resistor.

5. Process according to claim 4, in which the heating resistor and the associated temperature sensor are constructed of polysilicon or metal or silicon implanted using integrated circuit technology in one silicon substrate.

6. Process according to claim 4, in which a heating resistor of a suitable shape to receive and contain the said quantity of water/alcohol solution under investigation is used.

7. Process according to claim 6, in which a recess intended to receive and contain the said quantity of solution is constructed in the heating resistor, the said temperature sensor being located in the bottom of the said recess.

8. Process according to claim 1, in which the weight of the quantity of water/alcohol solution is measured while it is heated and evaporated.

9. Equipment for determining the alcoholic strength of a water/alcohol solution comprising:
    a heating device capable of receiving a predetermined quantity of the said water/alcohol solution,
    means for the supply of power, detection and control associated with the heating device and capable of activating the said heating device in a controlled way to cause heating of the said quantity of solution up to partial or complete evaporation, and to determine the total energy necessary during heating and evaporation of the said quantity to bring about partial or complete evaporation of the said quantity of solution, or the time required for partial or complete evaporation, or the integral of the said temperature over time or during partial or complete evaporation, wherein the magnitude of the determined parameters is indicative of the alcohol concentration by volume in the water/alcohol solution.

10. Equipment according to claim 9, comprising a capillary conduit having a predetermined diameter capable of permitting the deposition of a predetermined quantity of solution onto the heating device.

11. Equipment according to claim 9, in which the heating device comprises a heating resistor and the said means for the supply of power, detection and control are capable of providing power to the said resistor at a constant electrical power and of evaluating the total energy necessary to cause partial or complete evaporation of the said quantity of solution by detecting the change in the temperature of the said resistor over time during the period of time between starting to heat the said quantity of solution and partial or complete evaporation of the said quantity of solution.

12. Equipment according to claim 11, in which a temperature sensor such as a thermistor or a thermocouple is associated with the said heating resistor.

13. Equipment according to claim 12, in which the heating resistor and the associated temperature sensor are constructed for example of polysilicon, metal and the like using integrated circuit technology in the same silicon substrate.

14. Equipment according to claim 12, in which the heating resistor is of a shape adapted to receive and contain a quantity of the water/alcohol solution under investigation.

15. Equipment according to claim 14, in which a recess intended to receive and contain the said quantity of solution is constructed in the heating resistor, the aforesaid temperature sensor being located in the bottom of the said recess.

16. Equipment according to claim 9, comprising weighing means capable of detecting the weight of the quantity of water-alcohol solution under investigation while it is being heated and evaporated.

* * * * *